(12) United States Patent
Sugama

(10) Patent No.: US 6,595,361 B2
(45) Date of Patent: Jul. 22, 2003

(54) CONTAINER FOR HOLDING THEREIN NEEDLES USED IN SURGICAL OPERATION, CONTAINING INSTRUMENT FOR HOLDING THEREIN NEEDLES, AND PICKING DEVICE FOR USE IN CONTAINING NEEDLES

(76) Inventor: Kenji Sugama, 5-3, 3-chome Fujisaki, Kawasaki-ku, Kawasaki-shi, Kanagawa-ken (JP)

( * ) Notice: Subject to any disclaimer, the term of this patent is extended or adjusted under 35 U.S.C. 154(b) by 37 days.

(21) Appl. No.: 10/012,050

(22) Filed: Dec. 11, 2001

(65) Prior Publication Data

US 2002/0088728 A1 Jul. 11, 2002

(30) Foreign Application Priority Data

Dec. 11, 2000 (JP) .................................... 2000-375679
Dec. 6, 2001 (JP) .................................... 2001-372664
Dec. 6, 2001 (JP) .................................... 2001-372665

(51) Int. Cl.$^7$ ............................................. B65D 85/20
(52) U.S. Cl. ........................ 206/350; 206/383; 206/366
(58) Field of Search ................................. 206/363, 365, 206/366, 370, 63.3, 380, 382, 383, 350; 220/908, 910

(56) References Cited

U.S. PATENT DOCUMENTS 3,944,069 A * 3/1976 Eldridge, Jr. ............... 206/350
4,936,449 A * 6/1990 Conard et al. .............. 206/366
5,538,132 A * 7/1996 Propp et al. ................ 206/365

* cited by examiner

Primary Examiner—Jacob K. Ackun
(74) Attorney, Agent, or Firm—Arent Fox Kintner Plotkin & Kahn (57) ABSTRACT

A plastic sheet is formed into an upper sheet and a lower sheet. The lower sheet has on its inner surface a first pressure sensitive adhesive double coated tape. The upper sheet has a second pressure sensitive adhesive double coated tape on an edge portion. Magnetic rubber pieces are disposed on an upper or lower surface of the first tape. Laminated foamed members are disposed on a supporting member. A cover sheet is disposed on a side surface and on an upper surface of each of the foamed members. Numerals are indicated near, or on the upper surface of, the magnetic rubber pieces or the laminated foamed members. A picking device has a forward end portion and a handle portion. The forward end portion forms an angle of 30° through 35° relative to the handle portion. A magnetic rubber piece is disposed on a rear side of the forward end portion, and a conical projection is disposed on a front side of the forward end portion.

15 Claims, 4 Drawing Sheets

CONTAINER FOR HOLDING THEREIN NEEDLES USED IN SURGICAL OPERATION, CONTAINING INSTRUMENT FOR HOLDING THEREIN NEEDLES, AND PICKING DEVICE FOR USE IN CONTAINING NEEDLES

BACKGROUND OF THE INVENTION

1. Field of the Invention

This invention relates to a container for holding therein needles used in a surgical operation, a containing instrument for holding therein needles used in a surgical operation, as well as a picking device for picking needles for use in a surgical operation.

2. Description of Related Art

Regarding the needles for use by the doctors in carrying out suturation or paracentesis in a surgical operation, it is normal practice in many cases to count the number of needles prepared in advance for the surgical operation and to dispose respective needles in a container upon completion of the saturation or paracentesis, and to count the number of the needles upon completion of the surgical operation. After confirmation in this manner to see that the two numbers are in agreement with each other, the used needles are disposed of in a lump. Since many of the needles for a surgical operation are small and pointed, they are likely to get lost if they are merely placed inside a container. As a result, there are cases where the number of needles counted before the surgical operation does not coincide with the number counted after the operation. Further, when one is going to place the needles inside the container, one sometimes gets hurt by the needles. Therefore, when the patients of C type hepatitis and patients infected with AIDS virus are operated upon, there is a possibility that the persons engaged in the surgical operation get infected with such diseases.

In addition, it is also normal practice to insert the needles for a surgical operation into a piece of sponge or cork after the surgical operation and, after the surgical operation, they are disposed of after confirmation of the number of the needles. The same kind of problems as the above are likely to occur in this case.

Simply keeping control over the needles for suturation or paracentesis by putting them in a container or by sticking them into sponge, or the like, will sometimes result in a problem of loss in needles. Therefore, it has been required to safely treat and keep under control the needles used in a surgical operation after suturation or paracentesis.

This invention has an object of providing: a container for holding therein needles used in a surgical operation, which enables a safe disposal and control of the needles after suturation or paracentesis; a containing instrument for holding therein needles used in a surgical operation; as well as a picking device for use in containing needles for a surgical operation.

SUMMARY OF THE INVENTION

In order to attain the above and other objects, the present invention is a container for holding therein needles used in a surgical operation. The container is made of a plastic sheet folded into an upper sheet and a lower sheet. The upper sheet constitutes a lid for the lower sheet. The lower sheet comprises: a side wall on each of three sides of the lower sheet; a first adhesive tape disposed on at least a part of an inner surface of the lower sheet exclusive of the side walls; a second adhesive tape disposed along an edge of at least one side of the upper sheet; a plurality of magnetic rubber pieces disposed on one of an upper side and a lower side of the first adhesive tape in parallel with, and at a predetermined distance from, each other; and a piece of releasing paper placed in position on the first adhesive tape which has disposed thereon or thereunder the magnetic rubber pieces. By employing the container as constituted above, the needles for a surgical operation used for suturation or paracentesis can be adhered to the first adhesive tape and the magnetic rubber pieces. It is therefore possible for the doctors and nurses to safely dispose or keep control over the needles for a surgical operation after using them in suturation or paracentesis, thereby preventing the needles from getting lost.

The container may further comprise a third adhesive tape disposed on a part of an outer surface of the lower sheet exclusive of the side walls.

Preferably, a mark for counting the needles used in a surgical operation is indicated along a longitudinal direction of at least one of the plurality of magnetic rubber pieces. The indication is made near a bottom surface of, on an upper surface of, or both near the bottom surface and on the upper surface of, the magnetic rubber piece.

Another container for holding therein needles used in a surgical operation according to this invention comprises: a plastic sheet having a side wall on four sides; an adhesive tape disposed on at least part of an inner surface of the plastic sheet exclusive of the side walls; a plurality of magnetic rubber pieces disposed on one of an upper side and a bottom side of the adhesive tape in parallel with, and at a predetermined distance from, each other; and a piece of releasing paper placed in position on the plastic sheet which has disposed thereon or thereunder the magnetic rubber pieces.

The container may further comprise a second adhesive tape disposed on a part of an outer surface of the plastic sheet.

Also in this container, preferably, a mark for counting the needles used in the surgical operation is indicated along a longitudinal direction of at least one of the plurality of magnetic rubber pieces. The indication is made near a bottom surface of, on an upper surface of, or both near the bottom surface and on the upper surface of, the magnetic rubber pieces.

A containing instrument for holding therein needles used in a surgical operation according to this invention comprises a supporting member, and at least one plastic foamed member of rectangular parallelepiped in shape fixed to a surface of the supporting member. The foamed member is made of a laminated body having a plurality of foamed materials adhered together with an adhesive agent along a longitudinal direction thereof, and is so constructed and arranged that, when needles used in a surgical operation are inserted into a longitudinal side surface of the foamed member, the needles are capable of being inserted through a layer of the adhesive agent.

Preferably, the foamed member comprises a cover sheet provided on a side surface opposite to an inserting side surface of the foamed member into which the needles used in the surgical operation are inserted as well as on an upper surface thereof, or only on the opposite side surface thereof such that, when the needles used in the surgical operation are inserted into the inserting side surface, the needles are prevented from projecting out of the opposite side surface or the upper surface.

Also in this containing instrument, preferably, a mark for counting the needles used in the surgical operation is indicated along a longitudinal direction of at least one of the foamed member. The indication is made near a bottom surface of, on an upper surface of, or both near the bottom surface and on the upper surface of, the foamed member.

Another containing instrument for holding therein needles used in a surgical operation according to this invention comprises a supporting member, and at least one foamed member of columnar or polygonal shape adhered to a surface of the supporting member. The foamed member is made of a laminated body having a plurality of foamed materials adhered together with an adhesive agent into a coaxial shape in cross section, and is so constructed and arranged that, when needles used in the surgical operation are inserted into a peripheral surface of the foamed member, the needles are capable of being inserted through a layer of the adhesive agent.

Also in this containing instrument, preferably, a mark for counting the needles used in the surgical operation is indicated along the peripheral surface of the foamed member near a bottom surface of, on an upper surface of, or both near the bottom surface and on the upper surface of, the foamed member.

A picking device for use in containing needles for a surgical operation into the container according to this invention is of a scoop shape having a predetermined length with a forward end portion for picking up the needles and a handle portion. The forward end portion is bent at an angle of 30° through 35° relative to the handle portion. The device comprises a magnetic rubber piece disposed on at least part of a rear side of the front end portion, and a conical projection disposed on a front side of the forward end portion. This picking device is used in containing the needles into the above-described container. The range of the angle is the most suitable range in easily picking up or holding the needles for a surgical operation. If the angle falls outside this range, it becomes difficult to hold the needles. The conical projection is useful in sorting the needles of different sizes mixed together. By employing the picking device as arranged above, the handling of the needles becomes easy.

BRIEF DESCRIPTION OF THE DRAWINGS

The above and other objects and the attendant advantages of the present invention will become readily apparent by reference to the following detailed description when considered in conjunction with the accompanying drawings wherein.

DETAILED DESCRIPTION OF PREFERRED EMBODIMENTS

Figure 1:
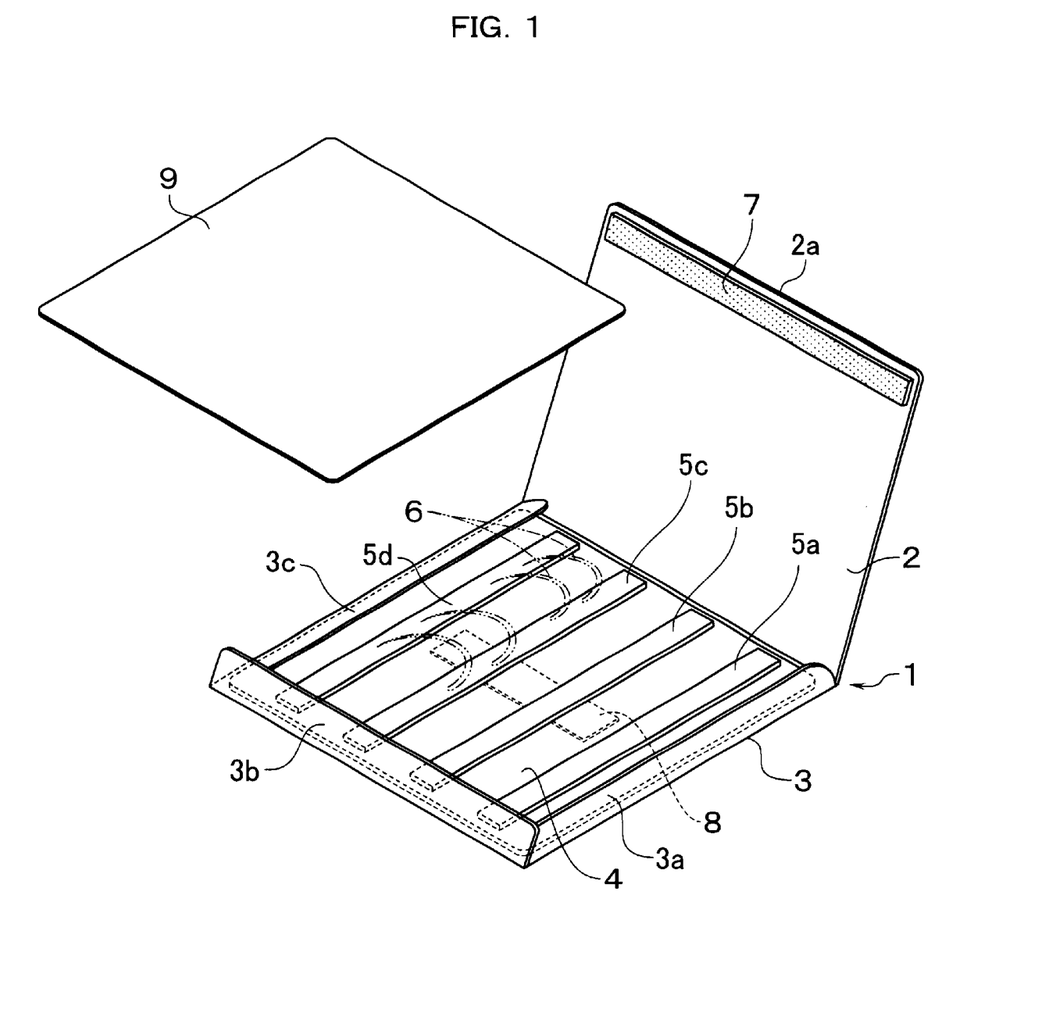
FIG. 1 is an exploded perspective view showing one example of arrangement of the container for holding therein needles according to this invention.

A container for holding therein needles used in a surgical operation according to embodiment 1 of this invention has the arrangement as shown in FIG. 1 and is manufactured in the following manner. As shown in FIG. 1, a plastic sheet 1 of a predetermined size is given a folding line in the center thereof to fold it into two, one of the folded sheets serving as an upper sheet 2 and the other serving as a lower sheet 3. The upper sheet 2 is constituted to serve as a lid to cover the lower sheet 3. The size of the lower sheet is arranged such that the three sides exclusive of the folded portion are larger than the size of the upper sheet 2. The portions thus projecting outward are folded inside so as to constitute side walls 3a, 3b, 3c, respectively. A first pressure sensitive adhesive double coated tape 4 with a piece of release paper is adhered to the entire inner surface of the lower sheet 3 other than the side walls 3a, 3b, 3c. After releasing this release paper, a plurality of magnetic rubber pieces (in FIG. 1, four magnetic rubber pieces 5a, 5b, 5c, 5d are shown as an example) are disposed on and adhered to the adhesive tape in parallel with each other at a predetermined distance from each other.

By arranging as shown in FIG. 1, the needles 6 that have been used for carrying out suturation of paracentesis in a surgical operation and are to be contained inside the container get firmly adhered to the first pressure sensitive adhesive double coated tape 4 or to the magnetic rubber pieces 5a through 5d inside the container and are prevented from dropping out of the container. Even if some needles get out of position for any reason, such needles 6 are prevented by the side walls 3a, 3b, 3c from dropping out of the container. This dropping is also prevented by covering the lower sheet 3 with the upper sheet 2. A second pressure sensitive addhesive double coated tape 7 with a release paper is adhered to an edge portion of at least one side, e.g., side 2a out of the three sides of the upper sheet 2. After containing the needles used for the surgical operation, the release paper is released and the upper sheet 2 is firmly adhered to the lower sheet 3. The upper sheet 2 will thus serve as a lid. By adhering a third pressure sensitive adhesive double coated tape 8 with a release paper to a part of the bottom outer surface of the lower sheet 3, the container is fixed to the position at which it is disposed while in use.

Further, if a piece of release paper 9 is disposed on the entire surface of the lower sheet 3 to which are adhered the magnetic rubber pieces 5a through 5d, and this release paper is released when put in use, the upper sheet 2 and the lower sheet 3 do not get adhered together before using the container. In addition, if this release paper is placed on top of the lower sheet 2 after having contained the needles in the container, the adhered needles are prevented from moving in position.

An arrangement may be made that a mark for counting the needles used in the surgical operation is indicated along a longitudinal direction near a bottom surface of at least one of the plurality of magnetic rubber pieces 5a through 5d. The indication may be made near a bottom surface of, on an upper surface of, or both near the bottom surface and on the upper surface of, at least one of the magnetic rubber pieces 5a through 5d, preferably on one or both of the magnetic rubber pieces 5a and 5d which are disposed on both ends. According to this arrangement, the number of needles contained inside the container can be easily confirmed. As the mark, anything will do as long as it serves the purpose of confirming the number of the needles. For example, numerals, alphabets, or the like may be used. In this case, the method of indicating the mark may be appropriately selected. For example, the mark may be directly printed on the upper surface of the rubber magnetic piece, or a sheet having indicated thereon the mark may be disposed in the longitudinal direction near the bottom surface of the magnetic rubber piece, or this sheet may be disposed on the upper surface of the magnetic rubber piece, or on both of them. Otherwise, the sheet having indicated thereon the mark may be disposed on an inner surface of the lower plastic sheet 1 exclusive of the side walls 3a, 3b, 3c.

The plastic sheet as the raw material for making the container of this invention is a transparent or translucent sheet made of plastic and is preferably the one which is capable of observing the contained needles with naked eyes. Although there is no particular limitation, as this kind of plastic, flexible plastic is preferable and polypropylene resin, polycarbonate resin or the like can be listed as examples.

The magnetic rubber piece to be used in this invention is of a sheet-like strip in which magnetic powders are kneaded into synthetic rubber and is available on the market (under the trade name of, e.g., FP MAG-X made by MAG-X Co., Ltd.). In disposing these magnetic rubber pieces in position, the magnetic rubber pieces are cut into predetermined sizes depending on the area of the lower sheet 3 so as to appropriately adhere them to the first pressure sensitive adhesive double coated tape 4 which has adhered preferably to the entire surface of the inner surface of the lower sheet 3 of the container. In case the size of the lower sheet is of the order of 10×10 cm, preferably the magnetic rubber pieces each of about 7 mm wide, about 90 mm long, and about 0.8 mm thick are disposed in parallel with each other at a constant distance from one another and are adhered. In this case, the number of the magnetic rubber pieces may be arbitrarily determined depending on the requirements of the doctors and nurses as well as depending on the contents of the surgical operation. The originally intended object can well be attained by adhering one through four magnetic rubber pieces with the above-described dimensions.

As the pressure sensitive adhesive double coated tape to be used in this invention, a product sold under the trade name of NITTO No. 500 (manufactured by NITTO DENKO Co., Ltd.) may be used.

Figure 2:
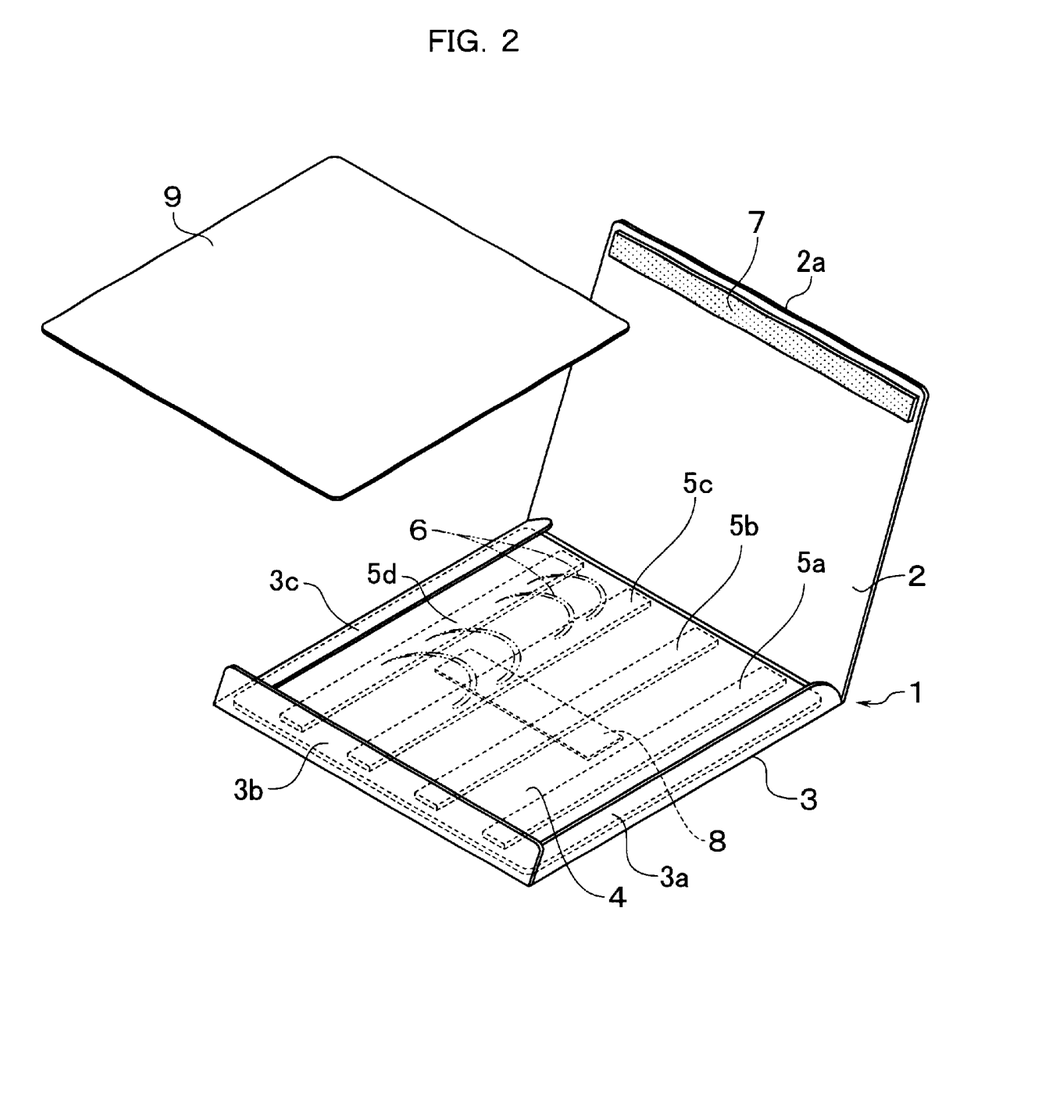
FIG. 2 is an exploded perspective view showing another example of arrangement of the container for holding therein needles according to this invention.

FIG. 2 shows embodiment 2 of the container for holding therein needles used in a surgical operation according to this invention. As shown in this example, a plurality of magnetic rubber pieces (in FIG. 2, four magnetic rubber pieces 5a, 5b, 5c, 5d are shown as an example) are placed on an inner surface of the lower sheet 3 and thereafter a pressure sensitive adhesive double coated tape 4 is adhered. The other arrangement and the method of manufacturing are the same as those shown in FIG. 1 with the same reference numerals being attached thereto.

Figure 3:
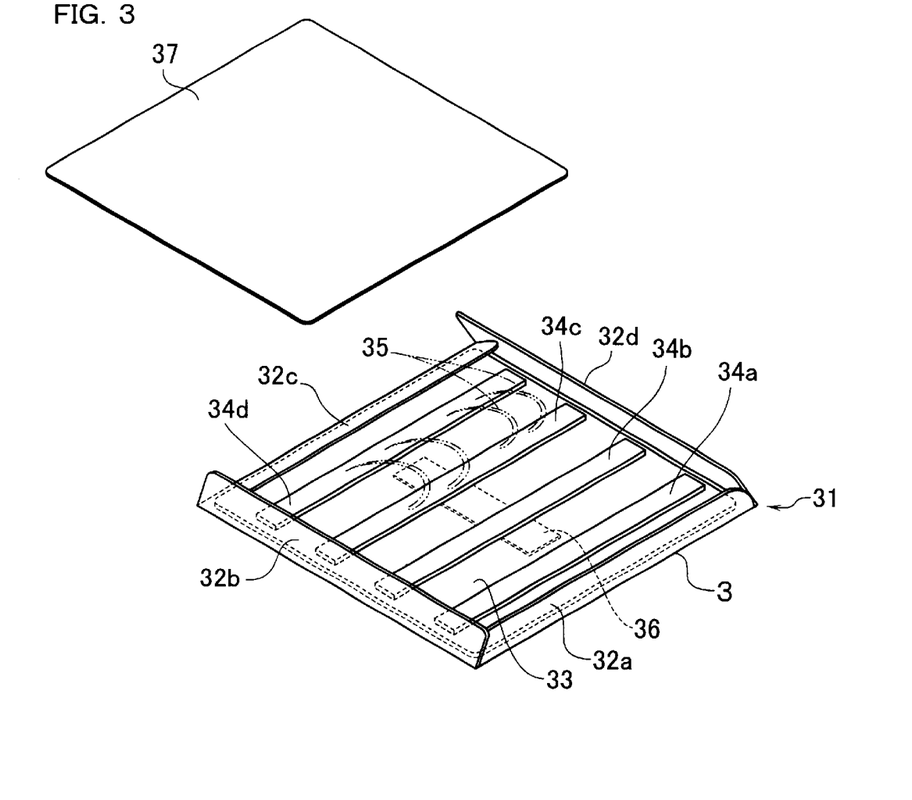
FIG. 3 is an exploded perspective view showing still another example of arrangement of the container for holding therein needles according to this invention.

FIG. 3 shows embodiment 3 of the container for holding therein needles used in a surgical operation according to this invention. The arrangement is the same as that shown in FIG. 1 except that there is no lid to the container and that there is one additional side wall. The container can be manufactured as follows in substantially the same manner as that shown with reference to FIG. 1.

A pressure sensitive adhesive double coated tape 33 with a piece of release paper attached thereto is adhered to the entire inner surface of a plastic sheet 31 except for the side wall portions 32a, 32b, 32c, 32d of the plastic sheet 31 of a regular dimension, and the release paper is peeled off. On top of this adhesive tape, a plurality of magnetic rubber pieces (in FIG. 3, four magnetic rubber pieces 34a, 34b, 34c, 34d are shown as example) are disposed in parallel with, and at a predetermined distance from, each other. Alternatively, in the same manner as the container shown in FIG. 2, the adhesive tape 33 may be adhered after the rubber magnetic pieces have been disposed.

By employing an arrangement as shown in FIG. 3, those needles 35 for a surgical operation after use in suturation or paracentesis which are to be contained in the container get firmly adhered to the pressure sensitive adhesive double coated tape 33 and/or to the magnetic rubber pieces 34a through 34d, whereby the needles are prevented from dropping outside. Further, even if the needles get out of position for any reason, the needles 35 are prevented by the side walls 32a through 32d from getting out of the container. In addition, by adhering a pressure sensitive adhesive double coated tape 36 with a piece of release paper to a part of the outer surface of the plastic sheet, the container can be fixed to a position where it is disposed when it is in use.

Further, on top of an entire surface of the plastic sheet to which are adhered the magnetic rubber pieces 34a through 34d, a piece of release paper 37 may be disposed so that this release paper is peeled off when in use. By employing this arrangement, the needles do not get adhered before use. Or else, after having contained the needles 35, this release paper may be disposed once again on top of the plastic sheet. Then, the adhered needles are prevented from moving in position.

An arrangement may also be made that a mark for counting the needles used in the surgical operation is indicated along a longitudinal direction of at least one of the plurality of magnetic rubber pieces. The indication may be made near a bottom surface of, on an upper surface of, or both near the bottom surface and on the upper surface of, at least one of the magnetic rubber pieces 34a through 34d, preferably on one or both of the magnetic rubber pieces 34a and 34d which are disposed on both ends. According to this arrangement, the number of needles contained inside the container can be easily confirmed. The method of indicating the mark is the same as that described above.

Figure 4:
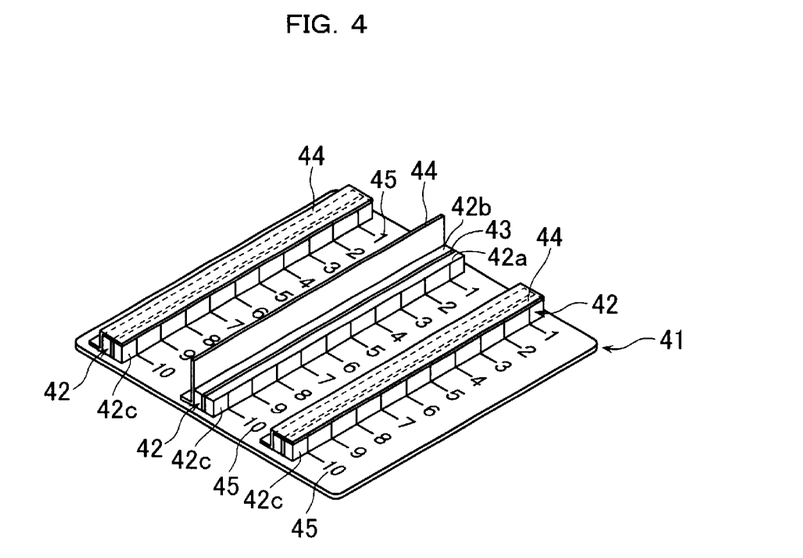
FIG. 4 is an exploded perspective view showing one example of arrangement of the containing instrument for holding therein needles according to this invention.

FIG. 4 shows a containing instrument for holding therein needles used in a surgical operation according to still another embodiment of this invention. On a surface of a supporting member 41, there are fixed foamed members 42 of rectangular parallelepiped in shape (in FIG. 4, three foamed members are shown as an example). Each of the foamed members 42 is made of a laminated body having two foamed materials 42a, 42b adhered together with an adhesive agent along a longitudinal direction thereof. When used needles are inserted into a longitudinal side surface 42c of the foamed member 42, the needles are inserted through the adhesive agent layer 43. In this arrangement, the needles do not get loose but are firmly fixed.

If the used needles project out of the surface opposite to the surface 42c or out of the upper surface when they are inserted into the side surface 42c of the foamed member 42, they may hurt the doctors or the nurses. To prevent such a problem, in the embodiment shown in FIG. 4, there is disposed a plastic cover sheet 44 on both the opposite side surface and the upper surface. This cover sheet 44 may be fixed only at the side surface while leaving it free on the upper surface. In FIG. 4, an example is shown in which the cover sheet 44 only on the foamed member in the center is in a state of being left open. The intended object may be attained without this cover sheet 44 depending on the material of the foamed member.

Along the longitudinal direction of the foamed member 42 near the lower surface thereof, there are indicated marks (numerals) 45 to count the number of the used needles so that the number of the contained needles can be easily confirmed. These numerals may be indicated on an upper surface of the foamed member 42 or may be indicated both near the lower surface and on the upper surface thereof. Any method of marking may be employed, such as directly printing the mark on the upper surface of the foamed member, or a sheet having printed thereon a mark may be disposed near the lower surface of, on an upper surface of, or both near the lower surface and on the upper surface of, the foamed member. Preferably, dividing lines are drawn along the indicated numerals. By employing this arrangement, the number of the inserted needles for the surgical operation can more easily be confirmed.

As the plastic foamed member 42 to be used in this embodiment, any flexible plastic foamed member will do as long as the needles for surgical operations can be easily inserted and be prevented from dropping out of position. For example, melamine foam made of a condensation polymer of melamine-formaldehyde, urethane foam, polyethylene foam, styrene foam, or the like, may be used. The dimensions of the foamed member 42 are not particularly limited; it may be of a size having a width for easily inserting therethrough the needles for surgical operations. Further, the material of the supporting member 41 is not particularly limited; a rigid plastic or cardboard will serve the purpose. The shape of the supporting member is not particularly limited; in order to facilitate the working, the supporting member may be provided with a handle.

Figure 5:
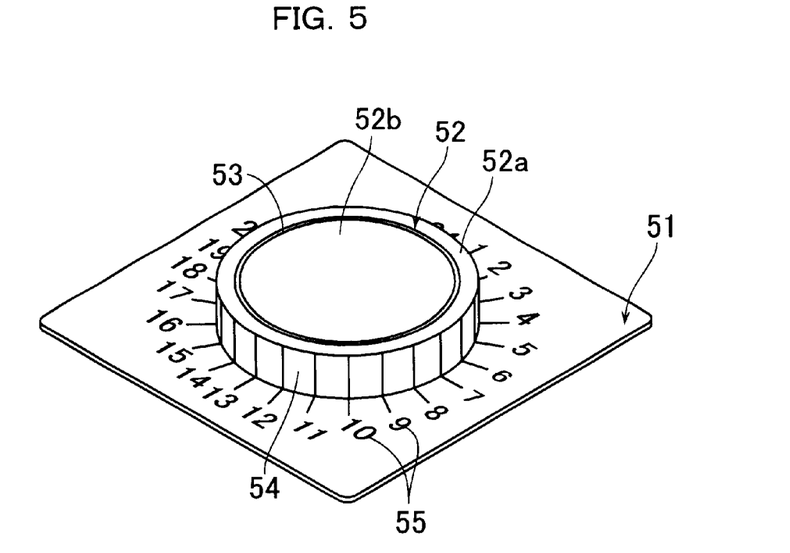
FIG. 5 is an exploded perspective view showing another example of arrangement of the containing instrument for holding therein needles according to this invention.

FIG. 5 shows still another embodiment of a containing instrument for holding therein needles used in a surgical operation according to this invention. In this embodiment, there is fixed with an adhesive agent a columnar plastic foamed member 52 on a supporting member 51. The foamed member 52 is a laminated body made by adhering foamed materials 52a and 52b with an adhesive agent into a coaxial column. An adhesive agent 53 is applied to the peripheral surface of the inner columnar plastic foamed member 52b and an outside plastic foamed member 52a is adhered by rolling in a manner to roll a band. Otherwise, a sheet of foamed member is punched into a coaxial columnar shape made up of the foamed material 52a and the foamed material 52b, and then both the materials may be adhered together with an adhesive agent.

The supporting member 51 may be made of a rigid plastic or a cardboard like in the example in FIG. 4. The shape of the supporting member is not particularly limited; in order to facilitate the working, the supporting member may be provided with a handle.

As the plastic foamed member 52, any flexible plastic foamed member will do as long as the needles for surgical operations can be easily inserted and be prevented from dropping out of position. The same foamed member as the above-described foamed member of rectangular parallelepiped may be used. The dimensions of the foamed member 52 are not particularly limited; it may be of a size having a diameter for easily inserting the needles for surgical operations. The needles used in the surgical operation are inserted along the periphery 54 of the foamed member 52.

Near the lower surface of the foamed member 52 along the peripheral surface 54 thereof, there are indicated marks (numerals) 55 to count the number of the used needles so that the number of the contained needles can be easily confirmed. These numerals may be indicated on an upper surface of the foamed member 52 or may be indicated both near the lower surface and on the upper surface. Any method of marking may be employed, such as directly printing the mark on the upper surface of the foamed member, or a sheet having printed thereon a mark may be disposed near the lower surface of, on an upper surface of, or both near the lower surface and on the upper surface of, the foamed member. Preferably, a plurality of vertical dividing lines are drawn along the peripheral surface 54 or radial dividing lines are drawn on the upper surface of the foamed member. By employing this arrangement, the number of the inserted needles for the surgical operation can more easily be confirmed.

As the shape of the foamed member, it may be of a columnar shape as shown in FIG. 5 or may be of a polygonal shape such as a triangular or a square column. This columnar shape also includes an elliptic shape.

Figure 6:
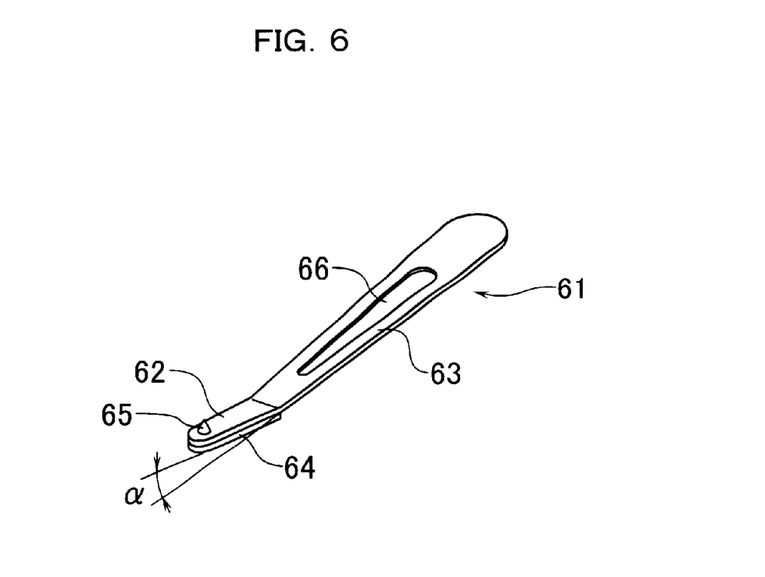
FIG. 6 is a perspective view showing an example of arrangement of a picking device for use in containing needles according to this invention.

A picking device for use in picking up needles for a surgical operation is used in containing the needles for a surgical operation into the above-described container or containing instrument. The needles for a surgical operation have different sizes inclusive of small ones. If the small needles are treated by pinching with fingers or pincers, it is time consuming and is accompanied by the fear of getting pricked with them. As shown in FIG. 6, the picking device 61 is a device of a spatula-like shape having a predetermined length made up of a forward end portion 62 and a handle portion 63. A magnetic rubber piece 64 is adhered to the rear side of at least a part of the forward end portion 62. This forward end portion 62 is bent at a predetermined angle, preferably in a manner to form an angle of alpha=30° through 35° relative to the handle portion 63. It is thus arranged that the needles can be held easily. If the angle falls out of this range, it becomes difficult to hold the needles. This magnetic rubber piece 64 may be adhered to the rear side of the forward end portion 62 in a manner projecting therefrom or may be adhered not to project therefrom by being buried in the forward end portion 62 in a manner to be flush with the handle portion 63. In addition, in case various sizes of needles are mixed together, it is possible to classify them into groups of the same size by using that conical projection 65 of a predetermined height which is disposed on the front side of the forward end portion 62. This projection can be used not only for the needles inside the container but also for the needles for a surgical operation which get scattered on the floor or on the operation bed. It may also be arranged that a recessed portion 66 of a predetermined size is provided in the central part of the handle portion 63 so that the handling of the picking device becomes easier.

According to the container for holding therein needles for a surgical operation, the needles used for suturation or paracentesis get firmly adhered to the pressure sensitive adhesive double coated tape and magnetic rubber pieces which are provided on the lower sheet in a manner not to drop outside the container. Even if the needles get out of adhesion, they are prevented from falling outside by the side walls of the lower sheet as well as by the upper sheet which serves the function of a lid. In addition, due to the pressure sensitive adhesive double coated tape provided on the outer surface of the lower sheet, the container is prevented from moving while in use. Still furthermore, since the release paper is provided on the lower sheet on which are disposed the magnetic rubber pieces, the upper sheet is prevented from getting adhered to the lower sheet. In addition, since there is indicated the mark for counting the used needles, the number of the contained needles can be easily confirmed.

According to another container of this invention having no plastic sheet lid, those needles for a surgical operation after suturation or paracentesis operation which are to be contained inside the container get firmly adhered to the pressure sensitive adhesive double coated tape disposed on the sheet and the magnetic rubber pieces so that they are prevented from falling outside. Even if they get out of position for any reason, the side walls of the sheet can prevent the needles from falling outside the container. In addition, due to the pressure sensitive adhesive double coated tape disposed on the outer surface of the sheet, the container does not move while in service. Still furthermore, since there is indicated a mark for counting the used needles, the number of the contained needles can be easily confirmed.

According to the containing instrument of this invention, since the used needles are inserted into the plastic foamed member having laminated a plurality of plastic foamed materials with an adhesive agent layer in between, the needles inserted to pierce this adhesive agent layer will be firmly fixed without getting loose. If the foamed member is of a rectangular parallelepiped, by disposing a cover sheet on the side opposite to the surface for inserting thereinto the needles, as well as on the upper surface, the needles are prevented from protruding outside the opposite side surface or the upper surface when inserted, thereby preventing the harms to the doctors and nurses. Still furthermore, since there is indicated a mark for counting the used needles, the number of the contained needles can be easily confirmed.

Further, according to the picking device for use in containing needles for a surgical operation into a container, it is possible to hold the needles for a surgical operation after use for saturation or paracentesis and is also possible to easily transport the above needles into the container and to contain them inside the container.

It is readily apparent that the above-described container for holding therein needles used in a surgical operation, a containing instrument for holding therein needles used in a surgical operation, as well as a picking device for picking needles used in a surgical operation meet all of the objects mentioned above and also have the advantage of wide commercial utility. It should be understood that the specific form of the invention hereinabove described is intended to be representative only, as certain modifications within the scope of these teachings will be apparent to those skilled in the art.

Accordingly, reference should be made to the following claims in determining the full scope of the invention.

What is claimed is:

1. A container for holding therein needles used in a surgical operation, said container being made of a plastic sheet folded into an upper sheet and a lower sheet, said upper sheet constituting a lid for said lower sheet, said lower sheet comprising:
    a side wall on each of three sides of said lower sheet;
    a first adhesive tape disposed on at least a part of an inner surface of said lower sheet exclusive of said side walls;
    a second adhesive tape disposed along an edge of at least one side of said upper sheet;
    a plurality of magnetic rubber pieces disposed on one of an upper side and a lower side of said first adhesive tape in parallel with, and at a predetermined distance from, each other; and
    a piece of releasing paper placed in position on said first adhesive tape which has disposed thereon or thereunder said magnetic rubber pieces.

2. The container according to claim 1, further comprising a third adhesive tape disposed on a part of an outer surface of said lower sheet exclusive of said side walls.

3. The container according to claim 1, wherein a mark for counting the needles used in a surgical operation is indicated along a longitudinal direction of at least one of said plurality of magnetic rubber pieces, said indication being made near a bottom surface of, on an upper surface of, or both near the bottom surface and on the upper surface of, said magnetic rubber piece.

4. The container according to claim 2, wherein a mark for counting the needles used in a surgical operation is indicated along a longitudinal direction of at least one of said plurality of magnetic rubber pieces, said indication being made near a bottom surface of, on an upper surface of, or both near the bottom surface and on the upper surface of, said magnetic rubber piece.

5. A container for holding therein needles used in a surgical operation, said container comprising:
    a plastic sheet having a side wall on four sides;
    an adhesive tape disposed on at least part of an inner surface of said plastic sheet exclusive of said side walls;
    a plurality of magnetic rubber pieces disposed on one of an upper side and a bottom side of said adhesive tape in parallel with, and at a predetermined distance from, each other; and
    a piece of releasing paper placed in position on said plastic sheet which has disposed thereon or thereunder said magnetic rubber pieces.

6. The container according to claim 5, further comprising a second adhesive tape disposed on a part of an outer surface of said plastic sheet.

7. The container according to claim 5, wherein a mark for counting the needles used in the surgical operation is indicated along a longitudinal direction of at least one of said plurality of magnetic rubber pieces, said indication being made near a bottom surface of, on an upper surface of, or both near the bottom surface and on the upper surface of, said magnetic rubber piece.

8. The container according to claim 6, wherein a mark for counting the needles used in the surgical operation is indicated along a longitudinal direction of at least one of said plurality of magnetic rubber pieces, said indication being made near a bottom surface of, on an upper surface of, or both near the bottom surface and on the upper surface of, said magnetic rubber piece.

9. A containing instrument for holding therein needles used in a surgical operation, said device comprising:
    a supporting member;
    at least one plastic foamed member of rectangular parallelepiped in shape fixed to a surface of said supporting member;
    said foamed member being made of a laminated body having a plurality of foamed materials adhered together with an adhesive agent along a longitudinal direction thereof, and being so constructed and arranged that, when needles used in a surgical operation are inserted into a longitudinal side surface of said foamed member, the needles are capable of being inserted through a layer of the adhesive agent.

10. The containing instrument according to claim 9, wherein said foamed member comprises a cover sheet provided on a side surface opposite to an inserting side surface of said foamed member into which the needles used in the surgical operation are inserted as well as on an upper surface thereof, or only on the opposite side surface thereof such that, when the needles used in the surgical operation are inserted into the inserting side surface, the needles are prevented from projecting out of the opposite side surface or the upper surface.

11. The containing instrument according to claim 9, wherein a mark for counting the needles used in the surgical operation is indicated along a longitudinal direction of at least one of said foamed member, said indication being made near a bottom surface of, on an upper surface of, or both near the bottom surface and on the upper surface of, said foamed member.

12. The containing instrument according to claim 10, wherein a mark for counting the needles used in the surgical operation is indicated along a longitudinal direction of at least one of said foamed member, said indication being made near a bottom surface of, on an upper surface of, or both near the bottom surface and on the upper surface of, said foamed member.

13. A containing instrument for holding therein needles used in a surgical operation, said device comprising:

a supporting member;

at least one foamed member of columnar or polygonal shape adhered to a surface of said supporting member;

said foamed member being made of a laminated body having a plurality of foamed materials adhered together with an adhesive agent into a coaxial shape in cross section, and being so constructed and arranged that, when needles used in the surgical operation are inserted into a peripheral surface of said foamed member, the needles are capable of being inserted through a layer of the adhesive agent.

14. The containing instrument according to claim 13, wherein a mark for counting the needles used in the surgical operation is indicated along the peripheral surface of said foamed member near a bottom surface of, on an upper surface of, or both near the bottom surface and on the upper surface of, said foamed member.

15. A picking device for use in containing needles for a surgical operation into the container as set forth in any one of claims 1 through 8, said device being of a spatula-like shape having a predetermined length with a forward end portion for picking up the needles and a handle portion, said forward end portion being bent at an angle of 30° through 35° relative to said handle portion, said device comprising a magnetic rubber piece disposed on at least part of a rear side of said forward end portion, and a conical projection disposed on a front side of said forward end portion.

* * * * *